(12) United States Patent
Chauhan

(10) Patent No.: US 10,302,609 B2
(45) Date of Patent: May 28, 2019

(54) CALIBRATION FOR GAS DETECTION

(71) Applicant: Detector Electronics Corporation, Minneapolis, MN (US)

(72) Inventor: Jitendra S. Chauhan, Eden Prairie, MN (US)

(73) Assignee: DETECTOR ELECTRONICS CORPORATION, Minneapolis, MN (US)

(*) Notice: Subject to any disclaimer, the term of this patent is extended or adjusted under 35 U.S.C. 154(b) by 207 days.

(21) Appl. No.: 15/116,436

(22) PCT Filed: Feb. 4, 2015

(86) PCT No.: PCT/US2015/014353
§ 371 (c)(1),
(2) Date: Aug. 3, 2016

(87) PCT Pub. No.: WO2015/119985
PCT Pub. Date: Aug. 13, 2015

(65) Prior Publication Data
US 2016/0349226 A1 Dec. 1, 2016

Related U.S. Application Data

(60) Provisional application No. 61/937,067, filed on Feb. 7, 2014.

(51) Int. Cl.
*G01N 33/00* (2006.01)
*G01N 21/27* (2006.01)
(Continued)

(52) U.S. Cl.
CPC ....... *G01N 33/0006* (2013.01); *G01N 21/274* (2013.01); *G01N 21/3504* (2013.01);
(Continued)

(58) Field of Classification Search
CPC . G01N 33/006; G01N 21/274; G01N 21/3504
See application file for complete search history.

(56) References Cited

U.S. PATENT DOCUMENTS

| 4,782,232 A | 11/1988 | Bernstein et al. |
| 5,060,505 A | 10/1991 | Tury et al. |

(Continued)

FOREIGN PATENT DOCUMENTS

| DE | 102012215594 B3 | 8/2013 |
| EP | 2192408 A1 | 6/2010 |

(Continued)

OTHER PUBLICATIONS

International Search Report and Written Opinion for application PCT/US2015/014353, dated Apr. 10, 2015, 11 pages.

*Primary Examiner* — Hezron Williams
*Assistant Examiner* — David Z Huang
(74) *Attorney, Agent, or Firm* — Cantor Colburn LLP

(57) ABSTRACT

Embodiments are directed to controlling a flow of a mixture of gas at a plurality of concentrations, controlling a temperature of a chamber over a temperature range, reading, by a computing device comprising a processor, gas absorbance values from a first detector included in the chamber over the plurality of concentrations and over the temperature range, generating at least one of a look-up table and a mathematical formula for the first detector based on the gas absorbance values, and causing the at least one of the look-up table and the mathematical formula to be stored in a second detector.

10 Claims, 4 Drawing Sheets

(51) Int. Cl.
*G01N 21/3504* (2014.01)
*G01N 21/03* (2006.01)

(52) U.S. Cl.
CPC ............ *G01N 21/0332* (2013.01); *G01N 2201/12753* (2013.01)

(56) References Cited

U.S. PATENT DOCUMENTS

| | | |
|---|---|---|
| 5,510,269 A | 4/1996 | Black et al. |
| 5,672,806 A | 9/1997 | Hung |
| 5,822,058 A | 10/1998 | Adler-Golden et al. |
| 5,892,229 A | 4/1999 | Crozier et al. |
| 6,098,013 A | 8/2000 | Mueller |
| 6,640,626 B2 | 11/2003 | Saikalis et al. |
| 6,916,664 B2 | 7/2005 | Bonne et al. |
| 6,967,485 B1 | 11/2005 | Hsueh et al. |
| 7,244,939 B2 | 7/2007 | Stuttard |
| 8,073,636 B2 | 12/2011 | Bauer et al. |
| 8,158,945 B2 | 4/2012 | Bitter et al. |
| 8,480,957 B2 | 7/2013 | Truex et al. |
| 2008/0264140 A1* | 10/2008 | Hill ............... G01N 33/0006 73/1.03 |
| 2009/0159798 A1 | 6/2009 | Weida et al. |
| 2012/0047995 A1 | 3/2012 | Fleischer et al. |
| 2012/0078532 A1 | 3/2012 | Forsyth et al. |
| 2013/0066564 A1 | 3/2013 | Forsyth |
| 2013/0209315 A1 | 8/2013 | Kimura |
| 2013/0293429 A1 | 11/2013 | Keller et al. |
| 2014/0278186 A1* | 9/2014 | Herzl ............... G01N 33/0006 702/104 |

FOREIGN PATENT DOCUMENTS

| | | |
|---|---|---|
| EP | 2635893 A2 | 9/2013 |
| WO | 2012059743 A2 | 5/2012 |

* cited by examiner

CALIBRATION FOR GAS DETECTION

BACKGROUND

One of the most difficult problems to overcome in designing and implementing a gas detector is the inconsistency in gas absorbance over an entire temperature range (e.g., −55 to +85 degrees Celsius). Multiple iterations of temperature testing and significant time are required to obtain correct absorbance values. This also imposes a limitation in terms of the detector's ability to support dynamic gas types or ranges.

Referring to FIG. 1A, a method 10 for populating gas correction tables is shown. In block 12, a temperature chamber is manually controlled to simulate many different ambient temperatures. In block 14, a designer or operator mixes many different gas concentrations. In block 16, a gas detection surface of the detector is populated manually for gas absorption at each temperature of block 12. In block 18, the detector's firmware is modified to feed the absorption values back into the detector or to change a formula to ensure that a correct gas concentration is calculated at each temperature.

The method 10 typically takes weeks to complete and may have to be repeated multiple times in order to gain confidence in the accuracy of the results. Moreover, detectors are typically limited to pre-defined gas types or ranges. Each time the designer wants to add a new gas type, or modify properties or parameters associated with a gas currently being monitored by a detector, the detector's firmware needs to be updated.

BRIEF SUMMARY

An embodiment is directed to a method comprising: controlling a flow of a mixture of gas in a chamber at a plurality of concentrations, controlling a temperature of the chamber over a temperature range, reading, by a computing device comprising a processor, gas absorbance values from a first detector included in the chamber over the plurality of concentrations and over the temperature range, generating at least one of a look-up table and a mathematical formula for the first detector based on the gas absorbance values, and causing the at least one of the look-up table and the mathematical formula to be stored in a second detector.

An embodiment is directed to an apparatus comprising: at least one processor, and memory having instructions stored thereon that, when executed by the at least one processor, cause the apparatus to: control a flow of a mixture of gas at a plurality of concentrations, control a temperature of a chamber over a temperature range, read gas absorbance values from a first detector included in the chamber over the plurality of concentrations and over the temperature range, and generate at least one of a look-up table and a mathematical formula based on the gas absorbance values.

An embodiment is directed to a system comprising: a chamber configured to be operated at a plurality of temperatures over a temperature range, a mass flow device configured to supply a mixture of gas to the chamber at a plurality of concentrations, a detector device configured to detect a concentration of the gas in the chamber, and a computing device configured to: read gas absorbance values from the detector device corresponding to applications of the gas in the chamber at the plurality of concentrations over the temperature range, and generate at least one of a look-up table and a mathematical formula as a file configured to be downloaded to an instance of the detector based on the gas absorbance values.

Additional embodiments are described below.

BRIEF DESCRIPTION OF THE DRAWINGS

The present disclosure is illustrated by way of example and not limited in the accompanying figures in which like reference numerals indicate similar elements.

DETAILED DESCRIPTION

Figure 1A:
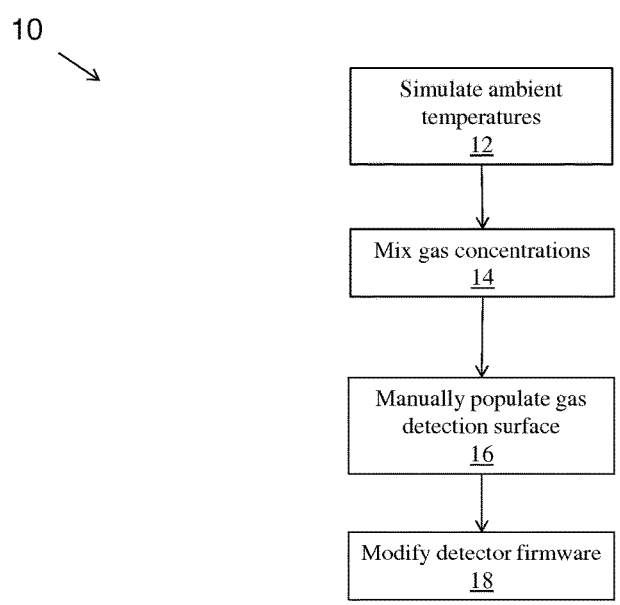
FIG. 1A is a flow chart of a method in accordance with the prior art.

It is noted that various connections are set forth between elements in the following description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

Exemplary embodiments of apparatuses, systems, and methods are described for automatically generating and programming a calibration surface (e.g., a standard calibration surface) of a detector (e.g., an optical gas detector). In some embodiments, automated processes may be used to collect data. An algorithm may be included in a detector. The algorithm, when executed, may enable the detector to learn the characteristics of any gas (e.g., hydrocarbon combustible gas, toxic gas, etc.), linearize the detector's response to that gas, and provide an accurate, open path gas detection output for the gas, potentially without requiring the detector to be re-certified or the detector's firmware to be modified.

Figure 1B:
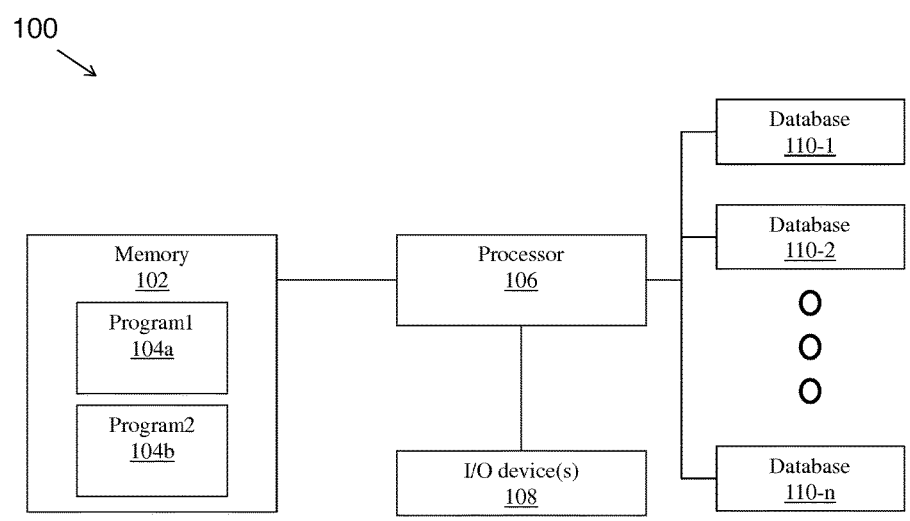
FIG. 1B is a schematic block diagram illustrating an exemplary computing system.

Referring to FIG. 1B, an exemplary computing system 100 is shown. Computing system 100 may be part of a detector. For example, at least a portion of the system 100 may be associated with firmware of the detector.

The system 100 is shown as including a memory 102. The memory 102 may store executable instructions. The executable instructions may be stored or organized in any manner and at any level of abstraction, such as in connection with one or more applications, processes, routines, procedures, methods, etc. As an example, at least a portion of the instructions are shown in FIG. 1B as being associated with a first program 104a and a second program 104b.

The instructions stored in the memory 102 may be executed by one or more processors, such as a processor 106. The processor 106 may be coupled to one or more input/output (I/O) devices 108. In some embodiments, the I/O device(s) 108 may include one or more of a keyboard or keypad, a touchscreen or touch panel, a display screen, a microphone, a speaker, a mouse, a button, a remote control, a control stick, a joystick, a printer, a telephone or mobile device (e.g., a smartphone), a sensor, etc. The I/O device(s) 108 may be configured to provide an interface to allow a user to interact with the system 100.

As shown, the processor 106 may be coupled to a number 'n' of databases, 110-1, 110-2, . . . 110-n. The databases 110 may be used to store data, such as data obtained from one or more sensors. In some embodiments, the data may pertain to one or more parameters associated with gas detection.

Figure 1C:
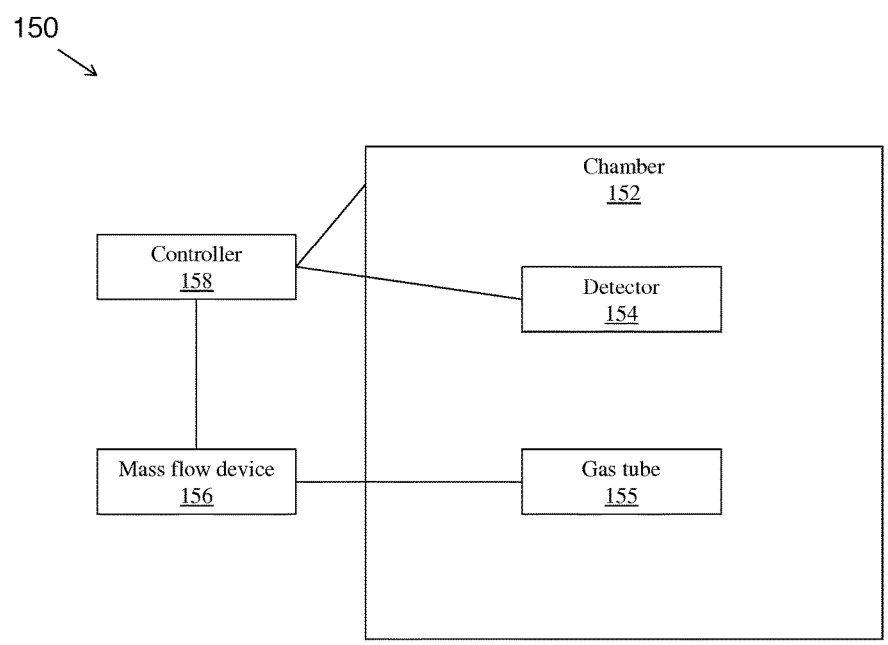
FIG. 1C is a block diagram of an exemplary system environment.

Referring now to FIG. 1C, a system 150 is shown. The system 150 may be associated with a test-bed or test equipment that may be used to populate or select values for a look-up table used in gas detection.

The system 150 may include a chamber 152. The chamber 152 may be a closed or partially closed structure. The chamber 152 may be used to control an environment in which a detector 154 is placed.

The detector 154 may represent an instance of a particular make and/or model of detector. The results of a test performed on the detector 154 may be applied to the detector 154 or other detectors (e.g., other instances of the detector 154).

The chamber 152 may include a gas tube 155. The gas tube 155 may be configured to be filled with one or more gases, potentially at one or more concentrations.

The gas tube 155 may be coupled to a mass flow device 156. The mass flow device 156 may mix one or more gases, at potentially one or more concentrations.

The mass flow device 156 may be controlled by, or operative in response to commands provided by, a computing device or controller 158. The controller 158 may control the temperature of the chamber 152. For example, the controller 158 may cause the temperature of the chamber 152 to sequence over a range of temperatures, potentially in discrete steps. The controller 158 may cause the mass flow device 156 to provide a sequence of concentrations of a gas over a range of concentrations to the gas tube 155.

At each temperature in the temperature sequence, the controller 158 may read from the detector 154 an absorbance value coinciding with the gas concentration dictated by the mass flow device 156. A look-up table or a mathematical formula may be generated by the controller 158 mapping the absorbance value to the gas concentration. One or more correction factors may be applied to account for any differences between the actual gas concentration output by the mass flow device 156/gas tube 155 and the gas concentration detected by the detector 154. Interpolation techniques (e.g., linearization techniques) may be used to generate data or values for temperatures or concentrations that were not applied to the detector 154 in the chamber 152.

The systems 100 and 150 are illustrative. In some embodiments, one or more of the entities may be optional. In some embodiments, additional entities not shown may be included. In some embodiments, the entities may be arranged or organized in a manner different from what is shown in FIGS. 1B-1C. For example, in some embodiments, the memory 102 may be coupled to or combined with one or more of the databases 110.

Embodiments of the disclosure may be used to automate data collection. In some embodiments, the data may be used to populate a calibration curve, surface, or look-up table. Parameters for gases may be added or modified. The parameters may be based on optical gas detection technology. In this respect, by populating or modifying a look-up table, firmware associated with a detector might not need to be modified for every type of gas, thereby removing the need to re-approve, re-certify, or re-test the firmware.

Figure 2:
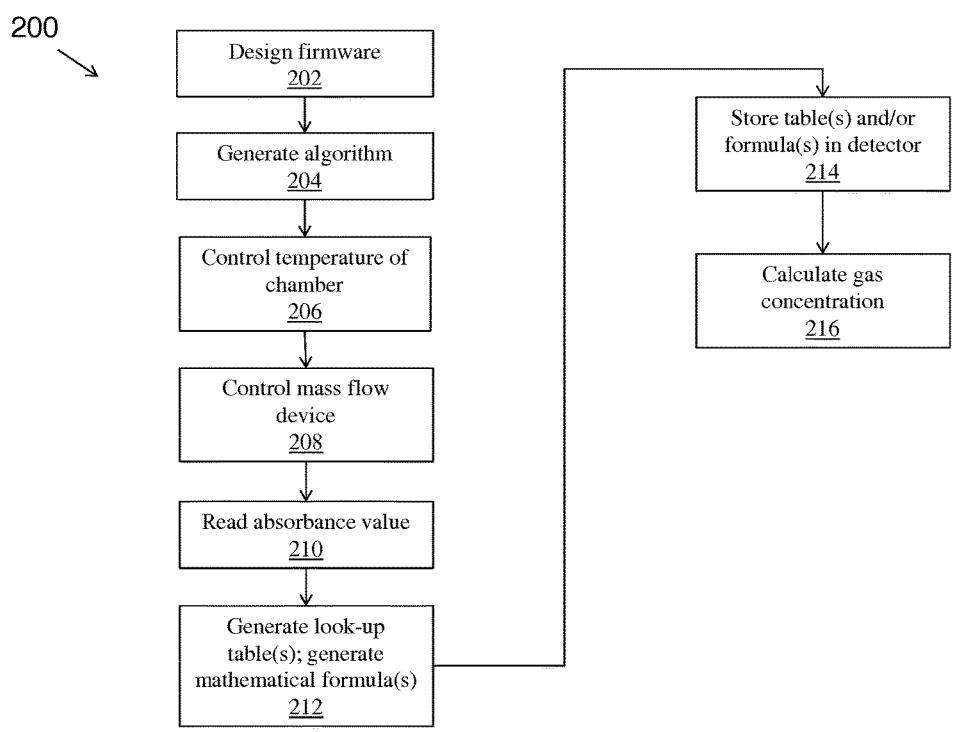
FIG. 2 illustrates a flow chart of an exemplary method.

Turning now to FIG. 2, a flow chart of an exemplary method 200 is shown. The method 200 may be at least partially executed by one or more systems, components, or devices, such as those described herein (e.g., the system 100). The method 300 may be used to populate a look-up table used in detecting gas.

In block 202, firmware for a detector may be designed. For example, the firmware may be designed to maintain a surface of gas absorbance values for an entire temperature range, potentially subject to modification using a communication interface.

In block 204, an algorithm may be generated. The algorithm may be configured to perform one or more tasks, such as those described below in connection with block 206-216.

In block 206, a temperature of a chamber may be controlled. For example, the temperature of the chamber may be set at a particular value.

In block 208, a mass flow device may be controlled. The mass flow device may mix a known or predetermined amount or concentration of gas or gases. For example, the mass flow device may provide for a flow of a single gas at a time, potentially at a plurality of concentrations.

In block 210, an absorbance value may be read from the detector. The reading performed in block 210 may be performed for each gas concentration and temperature.

In block 212, based on the value(s) read in block 210 one or more look-up tables may be generated. Additionally, or alternatively, one or more mathematical formulas for computing a gas concentration may be generated or modified. The look-up table and/or mathematical formulas may be organized as part of one or more files.

In block 214, the table(s) and/or formula(s) of block 212 may be stored in the detector. For example, the table(s) and/or formula(s) may be downloaded to the detector for purposes of storing the same. In some embodiments, the storage operation of block 214 may be performed by a manufacturer of the detector. In some embodiments, another party (e.g., a retailer or wholesaler, an end user or consumer, etc.) may perform the storage operation of block 214. For example, a manufacturer or supplier of the detector may provide a file that includes the table(s) and/or formula(s) for another party to download to the detector.

In block 216, the detector (e.g., the detector firmware) may calculate a gas concentration using one or more values from the look-up table(s) or one or more mathematical formulas. The detector may output the calculated gas concentration in one or more forms. In some embodiments, the output may include a warning indication if the detected gas concentration exceeds a threshold. In this manner, the detector may be used to warn of a hazardous gas condition.

The method 200 is illustrative. In some embodiments, one or more of the blocks or operations (or a portion thereof) may be optional. In some embodiments, one or more additional blocks or operations not shown may be included. In some embodiments, the blocks or operations may execute in an order or sequence that is different from what is shown in FIG. 2.

Embodiments of the disclosure may be used to automate the population of a look-up table or formula used in gas detection, thereby saving time and labor. In the event that a change or update is needed, such as when a (concentration of an) additional gas is to be detected by the detector, a look-up table or formula file may be generated to incorporate the change/update. The look-up table or formula file may subsequently be downloaded to the detector to facilitate the change/update. In this respect, the look-up table or formula may be used to supplement, and not replace, firmware associated with an instance of a detector.

As described herein, in some embodiments various functions or acts may take place at a given location and/or in connection with the operation of one or more apparatuses, systems, or devices. For example, in some embodiments, a portion of a given function or act may be performed at a first device or location, and the remainder of the function or act may be performed at one or more additional devices or locations.

Embodiments may be implemented using one or more technologies. In some embodiments, an apparatus or system may include one or more processors, and memory storing instructions that, when executed by the one or more processors, cause the apparatus or system to perform one or more methodological acts as described herein. Various mechanical components known to those of skill in the art may be used in some embodiments.

Embodiments may be implemented as one or more apparatuses, systems, and/or methods. In some embodiments, instructions may be stored on one or more computer-readable media, such as a transitory and/or non-transitory computer-readable medium. The instructions, when executed, may cause an entity (e.g., an apparatus or system) to perform one or more methodological acts as described herein.

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional.

What is claimed is:

1. A method comprising:
controlling, by a computing device comprising a processor, a flow of a mixture of gas in a chamber at a plurality of concentrations, wherein controlling the flow includes causing a mass flow device to provide a sequence of concentrations of the gas over a range of the plurality of concentrations to the chamber;
controlling, by the computing device, a temperature of the chamber over a temperature range, wherein controlling the temperature includes causing the temperature of the chamber to sequence over the temperature range;
reading, by the computing device, gas absorbance values from a first optical gas detector included in the chamber over the plurality of concentrations and over the temperature range, wherein the first optical gas detector includes a surface, wherein the first optical gas detector is associated with firmware, wherein the firmware is configured to cause the first optical detector to maintain the gas absorption values over the temperature range;
generating, by the computing device, a look-up table for the first optical gas detector based on the gas absorbance values, wherein generating the look-up table includes mapping, by the computing device, the gas absorption values read from the first optical gas detector to actual concentrations outputted by the mass flow device, wherein the look-up table is configured as a file for download to a second optical gas detector, wherein the file is configured to supplement firmware of the second optical gas detector without replacing the firmware of the second optical gas detector; and
causing, by the computing device, the look-up table to be stored in the second optical gas detector.

2. The method of claim 1, further comprising:
applying a correction factor to the look-up table to account for a difference between an actual concentration of the gas as outputted by the mass flow device and a gas absorbance value read from the first optical gas detector.

3. The method of claim 1, wherein the second optical gas detector corresponds to an instance of the first optical gas detector.

4. The method of claim 1, wherein the second optical gas detector and the first optical gas detector are the same optical gas detector.

5. An apparatus comprising:
at least one processor; and
memory having instructions stored thereon that, when executed by the at least one processor, cause the apparatus to:
control a flow of a mixture of gas in a chamber at a plurality of concentrations, wherein the control of the flow includes causing a mass flow device to provide a sequence of concentrations of the gas over a range of the plurality of concentrations to the chamber;
control a temperature of the chamber over a temperature range, wherein the control of the temperature includes causing the temperature of the chamber to sequence over the temperature range;
read gas absorbance values from a first optical gas detector included in the chamber over the plurality of concentrations and over the temperature range, wherein the first optical gas detector includes a surface, wherein the first optical gas detector is associated with firmware, wherein the firmware is configured to cause the first optical detector to maintain the gas absorption values over the temperature range; and
generate a look-up table for the first optical gas detector based on the gas absorbance values, wherein generating the look-up table includes mapping, by the computing device, the gas absorption values read from the first optical gas detector to actual concentrations outputted by the mass flow device, wherein the look-up table is configured as a file for download to a second optical gas detector, wherein the file is configured to supplement firmware of the second optical gas detector without replacing the firmware of the second optical gas detector.

6. The apparatus of claim 5, wherein the instructions, when executed by the at least one processor, cause the apparatus to:
apply an interpolation technique to generate a value for at least one of a temperature and a concentration that was not applied to the first optical gas detector in generating the look-up table.

7. The apparatus of claim 6, wherein the interpolation technique comprises a linearization technique.

8. The apparatus of claim 5, wherein the instructions, when executed by the at least one processor, cause the apparatus to:
apply a correction factor to the look-up table to account for a difference between an actual concentration of the gas as outputted by the mass flow device and a gas absorbance value read from the first optical gas detector.

9. The apparatus of claim 5, wherein the second optical gas detector corresponds to an instance of the first optical gas detector.

10. The apparatus of claim 5, wherein the instructions, when executed by the at least one processor, cause the apparatus to:
control a flow of a mixture of a second gas at a second plurality of concentrations;
control the temperature of the chamber over a second temperature range;
read gas absorbance values corresponding to an application of the second gas from the first optical gas detector over the second plurality of concentrations and over the second temperature range; and generate a second look-up table based on the gas absorbance values corresponding to the application of the second gas.

\* \* \* \* \*